(12) United States Patent
Sjöholm et al.

(10) Patent No.: US 7,049,449 B2
(45) Date of Patent: May 23, 2006

(54) METHOD FOR THE PREPARATION OF LARICIRESINOL CYCLOLARICIRESINOL AND SECOISOLARICIRESINOL

(75) Inventors: Rainer Sjöholm, Piispanristi (FI); Patrik Eklund, Turku (FI); Jyri-Pekka Mikkola, Turku (FI)

(73) Assignee: Hormos Medical Corporation, Turku (FI)

( * ) Notice: Subject to any disclaimer, the term of this patent is extended or adjusted under 35 U.S.C. 154(b) by 18 days.

(21) Appl. No.: 10/499,478

(22) PCT Filed: Jan. 7, 2003

(86) PCT No.: PCT/FI03/00005

§ 371 (c)(1),
(2), (4) Date: Jun. 18, 2004

(87) PCT Pub. No.: WO03/059340

PCT Pub. Date: Jul. 24, 2003

(65) Prior Publication Data

US 2005/0020673 A1   Jan. 27, 2005

(30) Foreign Application Priority Data

Jan. 17, 2002   (FI) .................................. 20020088

(51) Int. Cl.
*C07D 307/12*   (2006.01)
*C07D 313/04*   (2006.01)

(52) U.S. Cl. ...................... 549/502; 568/633; 568/644; 568/652

(58) Field of Classification Search ................ 549/502; 568/633, 644, 652
See application file for complete search history.

(56) References Cited

U.S. PATENT DOCUMENTS 6,372,922 B1 * 4/2002 Chattopadhyay et al. ... 549/502

FOREIGN PATENT DOCUMENTS

| JP | 02-040323 | 2/1990 |
| WO | WO 97/14670 | 4/1997 |
| WO | WO 00/59946 | 10/2000 |

OTHER PUBLICATIONS

Umezawa et al, "Synthesis of lariciresinols", (1994) vol. 121 No. 157395, abstract best avaiible.*
Freudenberg et al., "Die Lignane Des Fichtenholzes," 90 *Chemische Berichte Jahrg.* 2857-2869 (1957).
Okunishi et al., "Enantiomeric Compositions and Biosynthesis of Wikstroemia Sikokiana Lignans," 46 *J. Wood Sci* 234-242 (2000).
Moritani et al., "A Highly Stereoselective Synthesis of 3-hydroxy-1-aryltetralin Lignans Based on the Stereoselective Hydroxylation of α,β-dibenzyl-γ-butyro-lactones: The First Synthesis of (±)-cycloolivil," 1 *J. Chem. Soc., Perkin Trans.* 2747-2753 (1996).
Buckleton et al., "Oxidative Coupling of Lignns, II* Non-Phenolic Coupling of Diarylbutane Lignans Related to Matairesinol Dimethyl Ether," *Australian Journal of Chemistry* 305-324 (1987).
Kawamura et al., "Photodiscoloration of Western Hemlock (Tsuga Heterophylla) Sapwood III* Early Stage of Photodiscoloration Reaction with Lignans," 44 *J. Wood Sci* 47-55 (1998).

* cited by examiner

*Primary Examiner*—Kamal A. Saeed
(74) *Attorney, Agent, or Firm*—James C. Lydon

(57) ABSTRACT

A method for the preparation of lariciresinol, cyclolariciresinol or secoisolariciresinol, which method includes the steps of a) reducing hydroxymatairesinol to give 7-hydroxy-secoisolariciresinol, and b) subjecting the 7-hydroxy-secoisolariciresinol obtained in step a) to i) cyclization to give lariciresinol, or ii) cyclization to give cyclolariciresinol, or iii) catalytic hydrogenolysis to give secoisolariciresinol.

15 Claims, 1 Drawing Sheet

Figure 1:
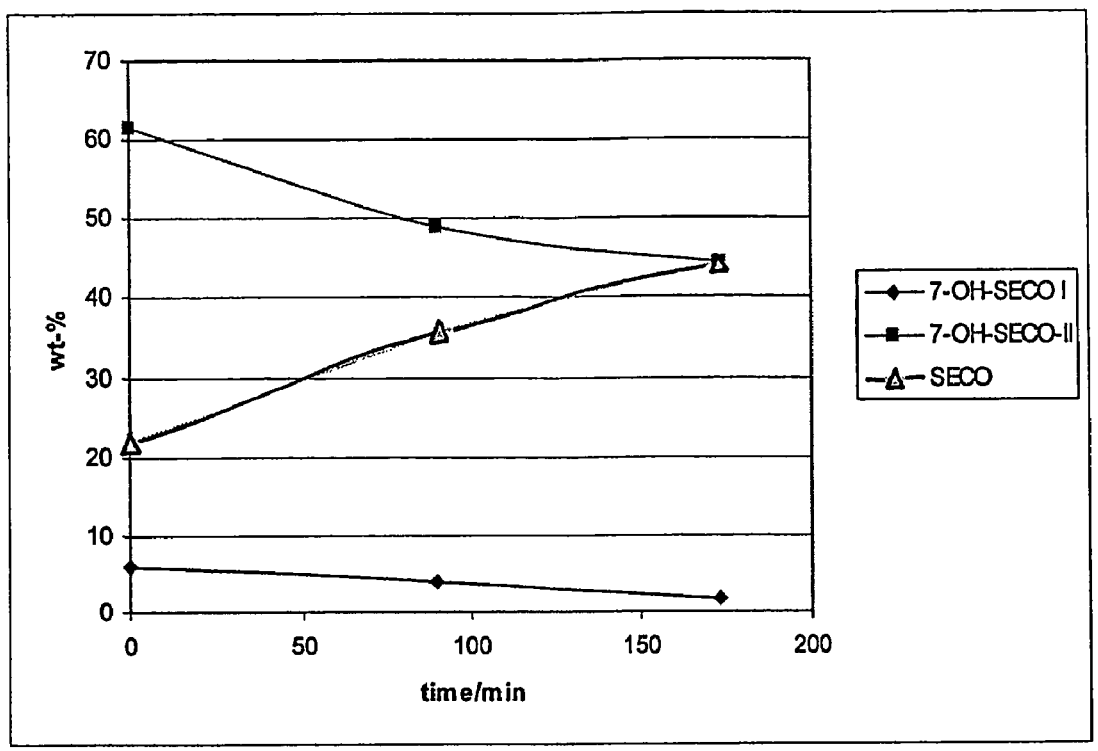

METHOD FOR THE PREPARATION OF LARICIRESINOL CYCLOLARICIRESINOL AND SECOISOLARICIRESINOL

This application is a U.S. National Stage of International application PCT/FI03/00005, filed Jan. 7, 2003.

FIELD OF THE INVENTION

This invention relates to the synthesis of the plant lignans lariciresinol, cyclolariciresinol or secoisolariciresinol from hydroxymatairesinol, as well as a novel intermediate.

BACKGROUND OF THE INVENTION

The publications and other materials used herein to illuminate the background of the invention, and in particular, cases to provide additional details respecting the practice, are incorporated by reference.

Lariciresinol, cyclolariciresinol (also called isolariciresinol) and secoisolariciresinol are all plant lignans known to possess valuable biological properties e.g. in cancer therapy. These lignans are also precursors for the mammalian lignans enterolactone and enterodiol.

Hydroxymatairesinol is also known as a biologically active plant lignan. Hydroxymatairesinol appears as two diastereomers, namely (−) hydroxymatairesinol (also denoted HMR 2 isomer) and (−) allo-hydroxymatairesinol (also denoted HMR 1 isomer).

Considerable amounts of lignans are found in coniferous trees. The type of lignans differs in different species and the amounts of lignans vary in different parts of the trees. The typical lignans in heart wood of spruce (*Picea abies*) are hydroxymatairesinol (HMR), a-conidendrin, conidendric acid, matairesinol, isolariciresinol, secoisolariciresinol, liovil, picearesinol, lariciresinol and pinoresinol (R. Ekman, "Distribution of lignans in Norway spruce", Acta Acad. Abo, Ser. B, 39:3, 1–6 (1979). The far most abundant single component of lignans in spruce is hydroxymatairesinol (HMR) (about 60 percent of total lignans) which occurs mainly in unconjugated free form. The lignan concentration in thick roots is 2–3 percent. Abundance of lignans occurs in the heart wood of branches (5–10 percent) and twists and especially in the knots, where the amount of lignans may be higher than 10 percent (R. Ekman, "Analysis of lignans in Norway spruce by combined gas chromatography—mass spectrometry", Holzforschung 30, 79–85 (1976); R Ekman 1979; Willfor, S., Hemming, J., Reunanen, M., Eckerman, C. and Holmbom, B. (2001): "Hydrophilic and lipophilic extractives in Norway spruce knots." Proc. 11$^{th}$ Inter. Symp. Wood Pulping Chem., ATIP, Nice.). These concentrations are about hundred-fold compared to ground flax powder known as a lignan-rich material.

It has been suggested to isolate hydroxymatairesinol from compression-wood fiber. These fibers originate from compression wood of stems and knots (oversized chip fraction) and they are known to weaken the quality of paper (R. Ekman, 1976; S. Willför et al. 2001).

It has recently been found that high amounts of hydroxymatairesinol can be produced by extracting finely divided wood material, preferably spruce knotwood, with a polar solvent or solvent mixture and precipitating hydroxymatairesinol from the extract as a complex. Suitable solvents to be used in the extraction step are, for example, pure ethanol or a mixture of ethanol and ethyl acetate. After the extraction step at least part of the solvent is preferably withdrawn before the addition of a complexing agent, which preferable is a carboxylate, such as acetate, of an alkali metal, such as potassium, an earth alkali metal, or ammonium. Such carboxylates form crystallisable adducts with hydroxymatairesinol. An especially preferable complexing agent is potassium acetate, which gives an easily crystallisable potassium acetate adduct of hydroxymatairesinol. This adduct is also rich in the (−) hydroxymatairesinol diastereomer.

SUMMARY OF THE INVENTION

It has now been found that hydroxymatairesinol, which can be derived from wood in great amounts, can be used as starting materials in the synthesis of lariciresinol, cyclolariciresinol or secoisolariciresinol.

This invention relates to a method for the preparation of lariciresinol, cyclolariciresinol or secoisolariciresinol. The method is characterized by the steps of a) reducing hydroxymatairesinol to give 7-hydroxy-secoisolariciresinol (Compound B in Scheme 1), and b) subjecting the 7-hydroxy-secoisolariciresinol obtained in step a) to i) cyclisation to give lariciresinol (Compound C in Scheme 1), or ii) cyclisation to give cyclolariciresinol (Compound D in Scheme 1), or iii) catalytic hydrogenolysis to give secoisolariciresinol (Compound E in Scheme 1).

The invention concerns also the novel compound 7-hydroxy-secoisolariciresinol, or a compound where said 7-hydroxy group is modified, for example esterified. The invention also includes the isomers of said compound.

DETAILED DESCRIPTION OF THE INVENTION

Hydroxymatairesinol appears as two diastereomers, namely (−) hydroxymatairesinol and (−) allo-hydroxymatairesinol. The word "hydroxymatairesinol", shall in the definition of this invention be understood to cover any pure geometric isomer or pure stereoisorner or any pure diastereomer or mixture of isomers or diastereomers of the compound. Salts, adducts and complexes of the compound shall also be understood to be covered by the term.

The reduction of hydroxymatairesinol to 7-hydroxy-secoisolariciresinol can in principle be carried out in different ways: by hydride addition, by catalytic hydrogenation, or reduction by metals such as Na or Zn in alcohols such as ethanol or 2-propanol. According to a preferable embodiment, the reduction is performed by LiAlH$_4$.

The novel compound 7-OH-secoisolariciresinot, obtained in step a), can, according to one alternative, be cyclised to lariciresinol by an intramolecular substitution of the 7-hydroxy group or a modified, such as an esterified, 7-hydroxy group by acid or base catalysed cyclisation. As acid catalysts Lewis acids, mineral acids or organic acids are suitable. As basic catalysts, metal hydroxides or alkoxides, organic bases such as amines or Lewis bases such as corresponding bases of organic or inorganic acids, can be used. Slow addition of an equimolar amount of acid or base is preferable.

According to another alternative, 7-OH-secoisolariciresinol can be cyclised to cyclolariciresinol. This can be performed in the same way as the cyclisation to lariciresinol described above, except that the use of excess acid is preferable.

According to a third alternative, 7-OH-secoisolariciresinol can be converted to secoisolariciresinol by catalytic hydrogenolysis of the 7- OH group, or a modified, such as esterified, 7-hydroxy group. The reaction is preferably carried out as a pressurized catalytic hydrogenolysis.

According to a preferable embodiment, the catalytic hydrogenolysis is a heterogenous catalysis.

A suitable catalyst is a metal or metal oxide or a mixture of metals and/or metal oxides. The catalyst can be either a metal or metal oxide powder, or the catalyst can be applied to a carrier. As suitable elements in the carrier can be mentioned Si, Al and C. The carrier can be, for example, solid particles such as powders, granules or extrudates.

The process can be carried out using any known reactor technology. It can thus be a slurry process where the catalyst particles are suspended in the liquid phase. Alternatively, a structured catalysis can be used. In this alternative, no filtration of the catalyst is needed. As examples of structured structured catalyses can be mentioned use of monolith technologies, packed columns, trickle-beds, Sulzer-type catalysts or fiber-bound catalysts.

Preferably, the catalyst is Pd, Pt, Ni, Rh, Ru, Co, a Raney-type catalyst such as Raney-Ni, or a oxide of the aforementioned elements. Mixtures of these metals and/or their oxides can also be used.

As especially suitable catalysts can be mentioned Raney-Ni or palladium on carbon (PdC).

In laboratory scale without any separate hydrogen source, the reaction can be carried out, for example, by use of Raney-Nickel catalyst in excess. In production scale, however, a separate hydrogen source (hydrogen gas) shall be used so as to reduce the amount of the expensive catalyst.

The term "pressurized hydrogenolysis" shall be understood to include any suitable pressure above normal atmosphere pressure, or the range about 2 to 200 bar. A preferable pressure range is, however, 5–70 bar, or even more preferably 15–70 bar.

The temperature is preferably kept in the range from 50 to 150° C.

As suitable solvents can be mentioned, for example, alcohols, esters, ethers, ketones, hydrocarbons or halogenated hydrocarbons. According to a preferred embodiment, the solvent is an alcohol such as ethanol, 2-propanol or a mixture thereof.

The invention will be illuminated by the following non-restrictive Experimental Section.

EXPERIMENTAL SECTION

Example 1

7-OH-secoisolariciresinol (Compound B in Scheme 1)

A mixture of (−)-allo-hydroxymatairesinol (4.5%) and (−)-hydroxymatairesinol (95.5%) (1.5 g, 4.017 mmol) was dissolved in dry THF (50 ml, freshly distilled over benzophenone and sodium metal). To the mixture was added portionwise LiAlH$_4$ (0.91 g, 24.021 mmol) over a period of 30 min at room temperature. The mixture was then slowly heated to 50° C. and stirred for 5 h under Ar. Then, the reaction mixture was poured onto saturated NaCl solution (200 ml) and neutralised with 10% HCl solution. The product was extracted with ethyl acetate (2×150 ml) and after addition of more NaCl to the aqueous phase, the mixture was further extracted with 100 ml EtOAc. The EtOAc fractions were combined and the solvent removed under reduced pressure. The product was crystallized from a mixture of EtOH and CHCl$_3$ (1:1), filtered and air-dried. Yield 1.18 g, 78%, isomeric ratio 4: 96%; mp. 149–151° C. (MeOH).

7-OH-secoisolariciresinol, Isomer II $\delta_H$ (500 MHz, Acetone d-6, 30° C.) 1.98 (1H, dddd, J=2.3, 6.0, 11.0 Hz, H-8), 2.21 (1H, m, H-8'), 2.47 (1H, dd, J=13.6, 7.6 Hz, H-7'a), 2.66 (1H, dd, J=13.6, 7.9 Hz, H-7'b), 3.52 (1H, dd, J=7.2, 11.0 Hz, H-9'b), 3.56–3.62 (2H, two double doublets overlapping, H-9'a, H-9b), 3.72 (3H, s, MeO'), 3.76 (3H, s, MeO), 3.78 (1H, dd, J=6.0, 11.0 Hz, H-9a), 4.91 (1H, d, J=6.0 Hz, H-7) 6.51 (1H, dd, J=7.9, 2.0 Hz, H-6'), 6.56 (1H, d, J=2.0 Hz, H-2'), 6.66 (1H, d, J=7.9 Hz, H-5'), 6.73 (1H, d, J=8.1 Hz, H-5), 6.75 (1H, dd, J=8.1, 1.6 Hz, H-6), 6.80 (1H, d, J=1.6 Hz, H-2). $\delta_C$ (125 MHz, Acetone d-6, 30° C.) 37.28 (C-7'), 41.11 (C-8'), 50.56 (C-8), 56.03 (OMe), 56.07 (OMe), 60.49 (C-9), 62.08 (C-9'), 73.87 (C-7), 110.54 (C-2), 113.13 (C-2'), 115.03 (C-5), 115.22 (C-5'), 119.65 (C-6), 122.41(C-6'), 133.32 (C-1'), 137.40 (C-1), 145.45 (C-4'), 145.99 (C-4), 147.90 (C-3'), 148.07 (C-3). HRMS; m/z calculated for $C_{20}H_{26}O_7$ (M$^+$) 378.16785, found 378.16790.

7-OH-secoisolariciresinol, Isomer I $\delta_H$ (500 MHz, Acetone d-6, 30° C.) 1.83 (1H, m, H-8'), 1.86 (1H, m, H-8), 2.59 (1H, dd, J=13.7, 8.1 Hz, H-7'b), 2.70 (1H, dd, J=13.7, 6.6 Hz, H-7'a), 3.50–3.60 (2H, m, coupled to OH, H-9'a, H-9'b), 3.73 (3H, s, OMe'), 3.74 (3H, s, OMe), 3.83 (1H, m, coupled to OH, H-9a), 3.95 (1H, m, coupled to OH, H-9b), 4.87 (1H, broad dd, H-7), 6.54 (1H, dd, J=2.0, 8.0 Hz, H-6'), 6.61 (1H, d, J=2.0 Hz, H-2'), 6.69 (1H, d, J=8.0 Hz, H-5'), 6.70 (1H, dd, J=1.8, 8.0 Hz, H-6), 6.73 (1H, d, J=8.0 Hz, H-5), 6.75 (1H, d, J=1.8 Hz, H-2). $\delta_C$ (125 MHz, Acetone d-6, 30° C.) 36.97 (C-7'), 43.70 (C-8'), 48.81 (C-8), 55.87 (OMe), 55.92 (OMe), 60.48 (C-9), 62.60 (C-9'), 76.23 (C-7), 110.63 (C-2), 113.29 (C-2'), 114.97 (C-5), 115.31 (C-5'), 120.40 (C-6), 122.52 (C-6'), 133.39 (C-1'), 137.16 (C-1), 145.50 (C-4'), 146.39 (C-4), 148.07–148.1 (C-3, C-3').

Example 2

Synthesis of (+)-lariciresinol

To a stirred solution of 7-OH-secoisolariciresinol (500 mg, 1.32 mmol, isomeric ratio 12:88 I:II) in dry THF (50 ml), was added BF$_3$.Et$_2$O (50 µl, (47% BF$_3$) in 5 ml dry CH$_2$Cl$_2$) as 100 µl portions every half an hour, totally 1.2 ml. The mixture was heated to 50° C. and stirred under Ar for 60 h. The reaction was then quenched by adding 3 ml triethylamine and the mixture was poured into saturated NaCl solution (150 ml). The product was extracted with EtOAc (3×50 ml) and the EtOAc fractions were combined, washed with 50 ml water and dried over NaSO$_4$. The solvent was removed under reduced pressure and the residue chromatographed on a silica column (CHCl$_3$:MeOH, 99:1 v/v) yielding lariciresinol (400 mg, 84%, $[\alpha]^{24}_D$=26.2° (c=1.0, MeOH), purity by GC 98%) which was further crystallised from CHCl$_3$ as white small needles; mp. 169–171° C. (CHCl$_3$).

(+)-Lariciresinol $\delta_H$ (500 MHz, CDCl$_3$, 30° C.) 2.40 (1H, m, H-8), 2.54 (1H, dd, J=13.6, 10.7 Hz, H-7'b), 2.73 (1H, m, H-8'), 2.91 (1H, dd, J=13.6, 5.1 Hz, H-7'a), 3.74 (1H, dd, J=8.7, 6.3 Hz, H-9'a), 3.77 (1H, dd, J=10.5, 6.4 Hz, H-9a), 3.86 (3H, s, OMe'), 3.87 (3H, s, OMe), 3.90 (1H, dd, J=10.5, 7.3 Hz, H-9b), 4.05 (1H, dd, J=8.7, 6.4 Hz, H-9'b), 4.78 (1H, d, J=7.0 Hz, H-7), 6.68 (1H, d, J=2.0 Hz, H-2'), 6.69 (1H, dd, J=2.0, 8.5 Hz, H-6'), 6.80 (1H, dd, J=2.0, 8.1 Hz, H-6), 6.83 (1H, d, J=8.5 Hz, H-5'), 6.86 (1H, d, J=2.0 Hz, H-2), 6.86 (1H, dd, J=8.1 Hz, H-5). 1c (125 MHz, CDCl$_3$, 30° C.) 33.35 (C-7'), 42.44 (C-8'), 52.61 (C-8), 55.95 (OMe), 55.97 (OMe), 60.95 (C-9), 72.92 (C-9'), 82.86 (C-7), 108.37 (C-2), 111.25 (C-2'), 114.22 (C-5), 114.45 (C-5'), 118.78 (C-6), 121.22 (C-6'), 132.30 (C-1'), 134.82 (C-1), 144.05 (C-4'), 145.08 (C-4), 146.57 (C-3'), 146.67 (C-3). EIMS; m/z 360 (100%, M$^+$), 194 (24), 180(16), 151 (29), 137(76). HRMS; m/z calculated for C$_{20}$H$_{24}$O$_6$ (M$^+$) 360.157289, found 360.157600.

Example 3

Synthesis of (+)-cyclolariciresinol

7-OH-secoisolariciresinol (150 mg, 0.397 mmol, isomeric ratio 12:88 I:II) was dissolved in 20 ml THF and 100 µl BF$_3$.Et$_2$O (47% BF$_3$) was added. The mixture was stirred under Ar and heated to 50° C., simultaneously 100 µl BF$_3$.Et$_2$O was added after one hour and two hours. The reaction was stirred for totally 6 h and 50 ml EtOAc followed by 3 ml triethylamine was added. The mixture was then poured into 50 ml NaCl-solution and extracted with 50 ml EtOAc. The EtOAc fraction was washed with 50 ml water, dried with NaSO$_4$ and the solvent was removed under reduced pressure. The residue was precipitated from CH$_2$Cl$_2$ yielding cyclolariciresinol as a white powder (110 mg, 77%); mp. 151–153° C. (CH$_2$Cl$_2$). $[\alpha]^{24}_D$=44.2° (c=1.0, MeOH).

(+)-cyclolariciresinol $\delta_H$ (500 MHz, CDCl$_3$-Acetone-d6, 30° C.) 1.80–1.86 (1H, m, H-8), 1.98–2.06 (1H, m, H-8'), 2.72 (1H, dd, J=15.8, 4.7 Hz, H-7'a), 2.79 (1H, dd, J=15.8, 11.4 Hz, H-7'b), 3.47 (1H, dd, J=10.7, 5.4 Hz, H-9a), 3.68–3.78 (3H, dd, dd, d, overlapping, H-9'a, H-7(J=10.8 Hz), H-9b), 3.80 (3H, s, OMe), 3.83 (1H, dd, H-9'b), 3.84 (3H, s, OMe'), 6.24 (1H, s, H-5'), 6.33 (1H, s, OH'), 6.50 (1H, s, OH), 6.59 (1H, s, H-2'), 6.63 (1H, d, J=2.0 Hz, H-2), 6.63 (1H, dd, J=8.5, 2.0 Hz, H-6), 6.79 (1H, d, J=8.5 Hz, H-5). $\delta_C$ (125 MHz, CDCl$_3$-Acetone-d6, 30° C.) 33.28 (C-7'), 40.15 (C-8'), 47.86 (C-7), 48.13 (C-8) 55.79, 55.85 (2xMeO), 62.43 (C-9), 66.09 (C-9'), 110.59 (C-2'), 112.04 (C-2), 114.43 (C-5), 115.90 (C-5'), 122.28 (C-6), 127.57 (C-6'), 132.96 (C-1'), 137.34 (C-1), 143.87 (C-3'), 144.41 (C-4'), 145.23 (C-4), 147.02 (C-3). EIMS; m/z (TMS-ethers) 455, 437, 527, 209, 568, 558, 648 (M$^+$), 633.

Example 4

Synthesis of (+)-lariciresinol with Methanolic H$_2$SO$_4$ in THF

To a stirred solution of 7-OH-secoisolariciresinol in 25 ml THF (233 mg, 0.616 mmol isomeric ratio 12:88 III1) was added 200 µl 5% H$_2$SO$_4$ in MeOH. 1 hour later 200 µl 5% H$_2$SO$_4$ in MeOH was added again and the reaction was stirred for 1 h more. Then 2 ml triethylamine was added and the mixture was poured into saturated NaCl solution (50 ml) and extracted with EtOAc (3×50 ml). The EtOAc fractions were combined, dried over NaSO$_4$ and the solvent was removed under reduced pressure. The residue was chromatographed on a silica column (CHCl$_3$:MeOH, 99:1 v/v) yielding lariciresinol (185 mg, 83.4%). Purity by GC 98%.

Example 5

Synthesis of Secoisolariciresinol by Catalytic Hydrogenolysis of 7-OH-secoisolariciresinol An isothermal, laboratory scale, stainless steel pressure autoclave (no baffles) having an internal diameter of 64 mm and a length of 103 mm was filled with 100 g of HPLC-grade EtOH (ethyl alcohol) in which 0.5 g of the 7-OH-secoisolariciresinol (mixture of I and II) was dissolved. 0.5 g of commercial molybdenum promoted Raney nickel type (Activated metals) catalyst was inserted into the reactor vessel together with the reaction mixture and heating was switched on. The mixture was flushed with hydrogen (99.999% pure, AGA OH) a couple of times to remove oxygen from the vessel. During the heating period the stirrer was not engaged. After 10 minutes heating with an electrical coil the reactor (equipped with a cooling coil and temperature controller) reached the desired reaction temperature of 100° C. (373 K). The stirrer was switched on (1150 rpm) and this was considered the initial start of the hydrogenation batch. However, already at this stage the amount of formed secoisolariciresinol was >20 wt-%. The pressure was adjusted to 375 PSI (approx. 26 bar).

The reaction was allowed to proceed for 173 minutes and small amounts of samples were withdrawn from the reaction mixture at scheduled intervals for later analysis by means of GC (gas chromatography). It turned out that the amount of secoisolariciresinol obtained at this time was 44.36 wt-%. The samples (a few milliliters) were obtained through a 5 µm metallic sinter filter by cracking a sample valve, immediately wrapped into an aluminium folio to protect them from light exposure and transferred to a freezer (−20° C., 253 K).

After 173 minutes the initial secoisolariciresinol concentration of 21.9 wt-% increased to 44.36 wt-%, whereas the initial 7-OH-secoisolariciresinol content (7-OH-secoisolariciresinol 15.9 wt-%, 7-OH-secoisolariciresinol II 61.6 wt-%) was reduced to 1.6 and 44.5 wt-% (7-OH-Seco, 7-OH-Seco II). The concentration evolvement as a function of time is displayed in FIG. 1.

Example 6

Figure 2:
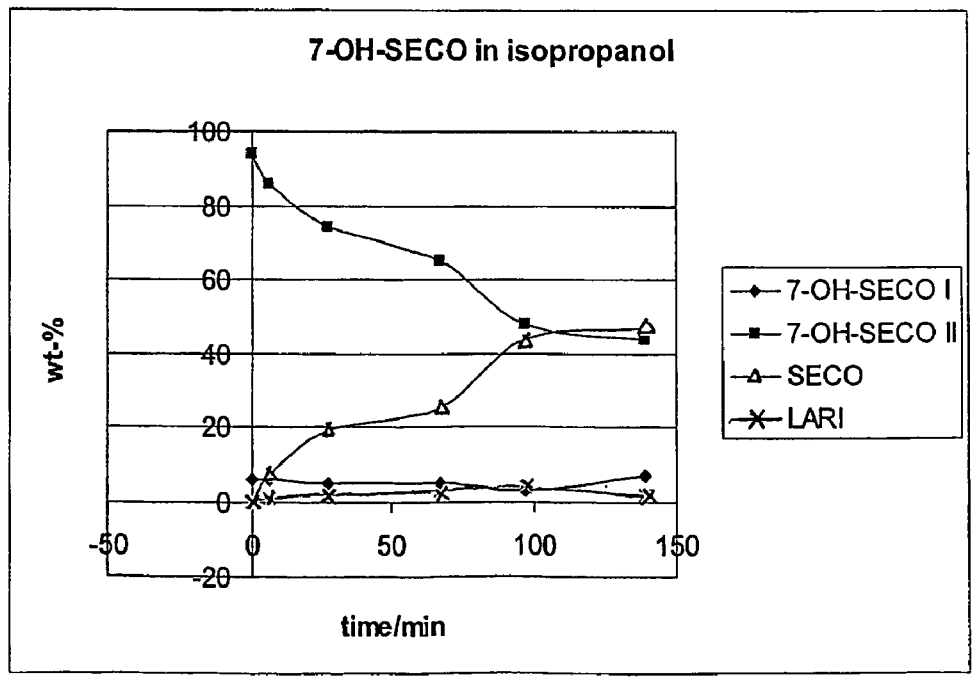

Synthesis of Secoisolariciresinol by Catalytic Hydrogenolysis of 7-OH-secoisolariciresinol The procedure described in Example 5 was repeated except that the following starting materials and conditions were used: 0.20 g of 7-OH-secoisolariciresinol; 100 g of 2-propanol; 0.4 g of Raney nickel catalyst; pressure 33–35 bar; and temperature 140° C. The concentration evolvement is shown in FIG. 2.

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

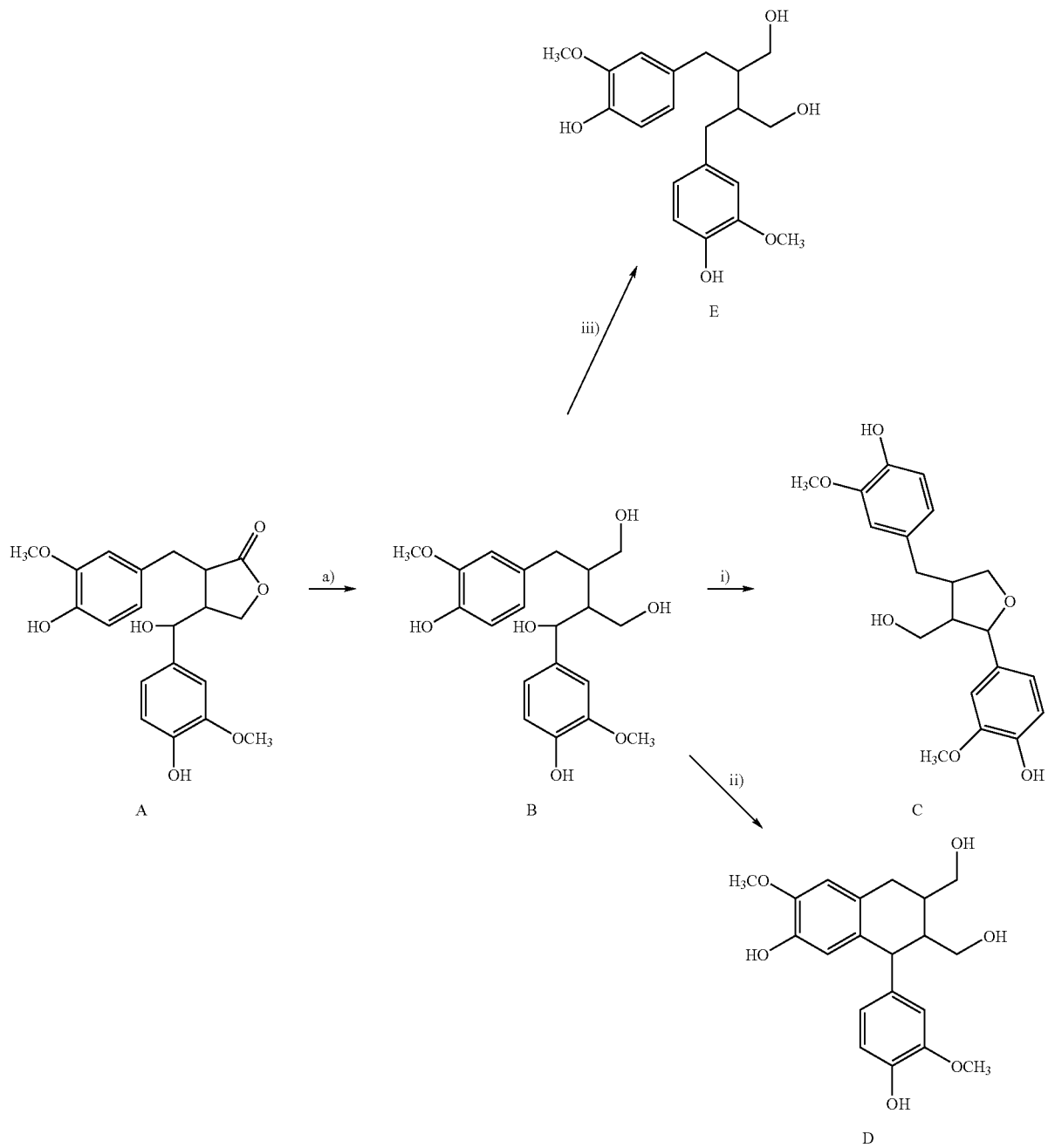

Scheme 1

The invention claimed is:
1. Method for the preparation of lariciresinol, cyclolariciresinol or secoisolariciresinol, comprising the steps of
   a) reducing hydroxymatairesinol to give 7-hydroxy-secoisolariciresinol, and
   b) subjecting the 7-hydroxy-secoisolariciresinol obtained in step a) to
      i) cyclisation to give lariciresinol, or
      ii) cyclisation to give cyclolariciresinol, or
      iii) catalytic hydrogenolysis to give secoisolariciresinol.

2. The method of claim 1, wherein the reduction of hydroxymatairesinol in step a) is performed by hydride addition, catalytic hydrogenation or by a metal.

3. The method of claim 1, wherein the reduction of hydroymatairesinol in step a) is performed by LiAlH$_4$.

4. The method of claim 1, wherein the 7-OH-secoisolariciresinol in step b) i) is cyclised to lariciresinol under acid-catalysed or base-catalysed conditions.

5. The method of claim 4, wherein the reaction is accomplished by use of $BF_3 \cdot EtO_2$ in $CH_2Cl_2$/THF, methanolic $H_2SO_4$ or aqueous HCl.

6. The method of claim 1, wherein the 7-OH-secoisolariciresinol in step b) ii) is cyclised to cyclolariciresinol under acid-catalysed conditions.

7. The method of claim 6, wherein the reaction is accomplished by use of $BF_3$, $EtO_2$; $H_2SO_4$; aqueous HCl or TFA.

8. The method of claim 1, wherein the 7-hydroxy group of the compound 7-hydroxy-secoisolariciresinol obtained in step a) is esterified, after which the ester is subjected to catalytic hydrogenolysis to give secoisolariciresinol.

9. The method of claim 1, wherein the catalytic hydrogenolysis in step b) iii) is carried out under pressurized conditions.

10. The method of claim 9, wherein the catalytic hydrogeriolysis is a heterogenous catalysis.

11. The method of claim 10, wherein the catalyst is a metal or metal oxide or a mixture of metals and/or metal oxides.

12. The method of claim 11, wherein the catalyst Pd, Pt, Ni, Rb. Ru, Co, a Raney catalyst, or an oxide of the aforementioned elements, or a mixture thereof.

13. A compound which is 7-hydroxy-secoisolariciresinol or an isomer thereof, or a comnound where said 7hydroxy group has been esterified.

14. The method of claim 6, wherein said 7-OH-secoisolariciresinol is cyclised using an excess of acid.

15. The method of claim 12, wherein said Raney catalyst is Raney nickel.

* * * * *